(12) United States Patent  
Davis et al.

(10) Patent No.: US 8,702,935 B2  
(45) Date of Patent: Apr. 22, 2014

(54) ELECTROCHEMICAL SENSORS INCLUDING ELECTRODES WITH DIFFUSION BARRIERS

(75) Inventors: Brian Keith Davis, Butler, PA (US); Towner Bennett Scheffler, Butler, PA (US); Michael Alvin Brown, Cranberry Township, PA (US)

(73) Assignee: Mine Safety Appliances Company, Cranberry Township, PA (US)

( * ) Notice: Subject to any disclaimer, the term of this patent is extended or adjusted under 35 U.S.C. 154(b) by 227 days.

(21) Appl. No.: 12/914,685

(22) Filed: Oct. 28, 2010

(65) Prior Publication Data

US 2011/0100813 A1  May 5, 2011

Related U.S. Application Data

(60) Provisional application No. 61/256,787, filed on Oct. 30, 2009.

(51) Int. Cl.  
*G01N 27/30* (2006.01)

(52) U.S. Cl.  
USPC ............. 204/415; 204/432; 204/282; 156/60; 205/782.5; 205/775

(58) Field of Classification Search  
USPC .................. 204/430–432, 400, 282, 415; 205/780.5, 782.5, 793, 775; 156/60  
See application file for complete search history.

(56) References Cited

U.S. PATENT DOCUMENTS

| | | | |
|---|---|---|---|
| 5,338,429 A * | 8/1994 | Jolson et al. | 204/415 |
| 5,944,969 A | 8/1999 | Scheffler | |
| 7,147,761 B2 * | 12/2006 | Davis et al. | 204/421 |
| 2005/0098447 A1 * | 5/2005 | Broy et al. | 205/775 |
| 2005/0145493 A1 * | 7/2005 | Saffell et al. | 204/431 |
| 2007/0102294 A1 | 5/2007 | Dorisio Deininger et al. | |

FOREIGN PATENT DOCUMENTS

WO  WO2011053721 A1  5/2011

OTHER PUBLICATIONS

Alphasense: Potentiostat Circuit for D2 Combined CO and H2S Sensor, extracted from www.alphasense.com, Mar. 2007, pp. 1-3.  
Cao, Z. and Stetter, J.R., The Properties and Applications of Amperometric Gas Sensors, Electroanalysis, (1992) 4(3), 253.

* cited by examiner

*Primary Examiner* — Jennifer Dieterle  
(74) *Attorney, Agent, or Firm* — Bartony & Associates, LLC

(57) ABSTRACT

An electrochemical gas sensor includes a housing, a first working electrode within the housing and having a first section of gas transfer medium and a first layer of catalyst on the first section of gas transfer medium, and at least a second working electrode within the housing and having a second section of gas transfer medium and a second layer of catalyst on the second section of gas transfer medium. At least one of the first section of gas transfer medium and the second section of gas transfer medium includes at least one area in which the structure thereof has been irreversibly altered to limit diffusion of gas through the at least one of the first section of gas transfer medium or the second section of gas transfer medium toward the other of the at least one of the first section of gas transfer medium and the second section of gas transfer medium.

20 Claims, 8 Drawing Sheets

Fig. 1B
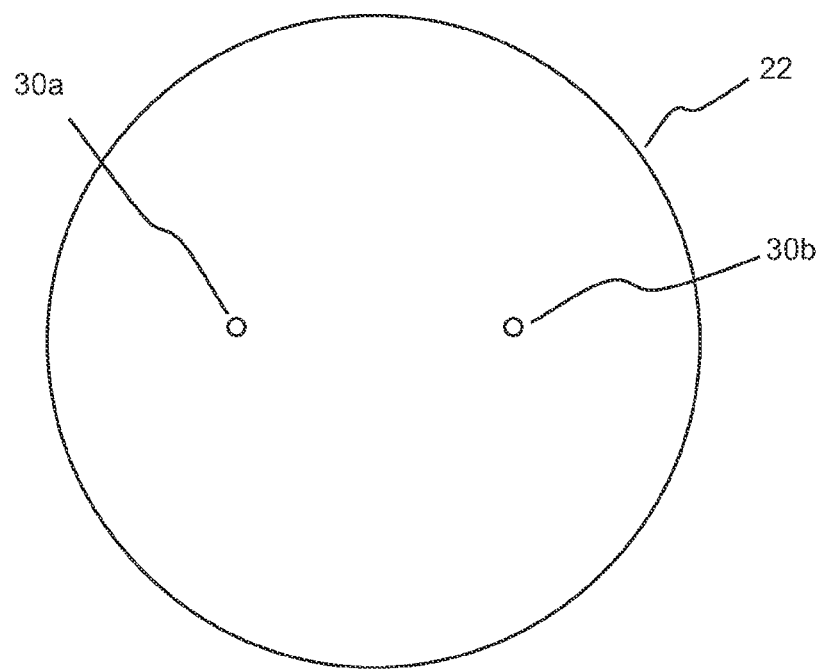
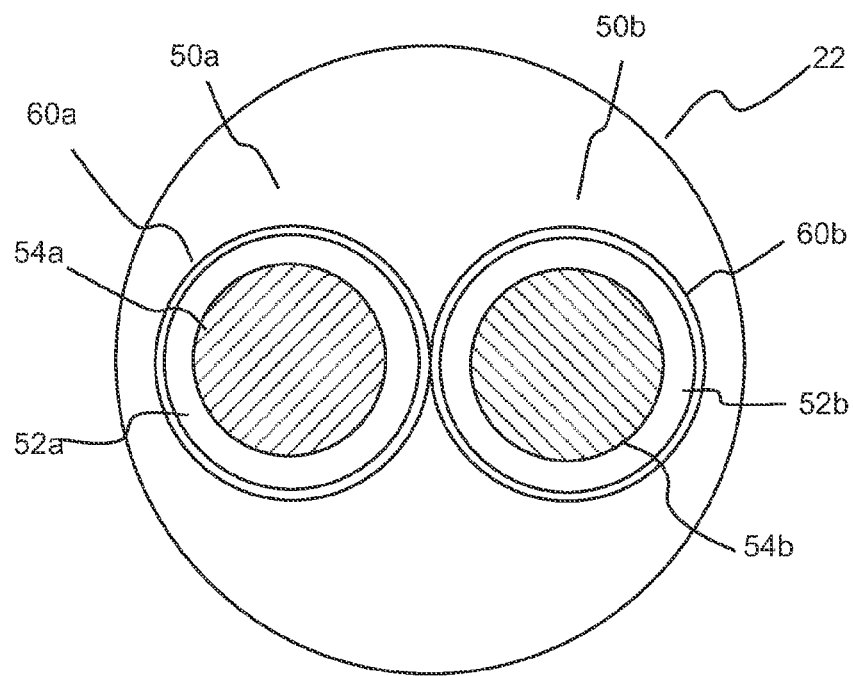
Fig. 1C

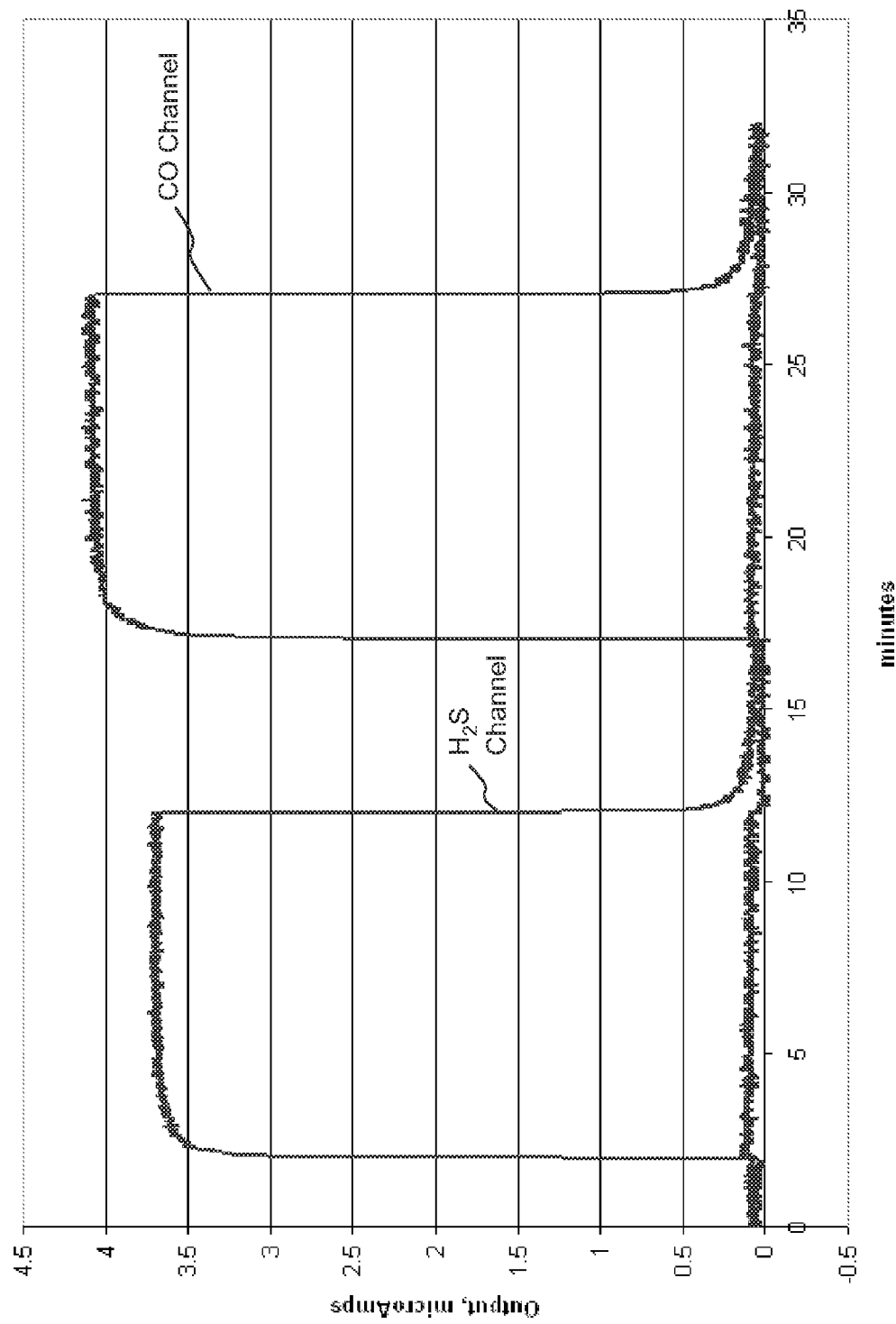

ELECTROCHEMICAL SENSORS INCLUDING ELECTRODES WITH DIFFUSION BARRIERS

CROSS-REFERENCE TO RELATED APPLICATION

This application claim benefit of U.S. Provisional Patent Application No. 61/256,787, the disclosure of which is incorporated herein by reference.

BACKGROUND

The terms used herein are not intended to be limited to any particular narrow interpretation unless clearly stated otherwise in this document. References set forth herein may facilitate understanding of the devices, systems and/or methods described herein or the background. The disclosure of any reference cited herein is incorporated by reference.

In an electrochemical gas sensor, the gas to be measured typically passes from the atmosphere into the sensor housing through a gas porous or gas permeable membrane to a first electrode known as a working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working electrode. A comprehensive discussion of electrochemical gas sensors is also provided in Cao, Z. and Stetter, J. R., "The Properties and Applications of Amperometric Gas Sensors," *Electroanalysis*, 4(3), 253 (1992), the disclosure of which is incorporated herein by reference.

To be useful as an electrochemical sensor, a working and counter electrode combination must be capable of producing an electrical signal that is (1) related to the concentration of the analyte gas and (2) sufficiently strong to provide a signal-to-noise ratio suitable to distinguish between concentration levels of the analyte gas over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte.

Electrical connection between the working electrode and the counter electrode is maintained through an electrolyte. Functions of the electrolyte include: (1) to efficiently carry the ionic current; (2) to solubilize the analyte gas; (3) to support both the counter and the working electrode reactions; and (4) to form a stable reference potential with the reference electrode. Criteria for an electrolyte can include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction reaction occurs to provide a mechanism whereby the ionic conduction of the electrolyte solution is coupled with the electron conduction of the electrode to provide a complete circuit for a current.

The measurable current arising from the cell reactions of the electrochemical cell is directly proportional to the extent of reaction occurring at the electrode. Preferably, therefore, a high reaction rate is maintained in the electrochemical cell. For this reason, the counter electrode and/or the working electrode of the electrochemical cell generally include an appropriate electrocatalyst on the surface thereof to support the reaction rate.

An electrochemical gas sensor in which two or more gas analytes are to be detected typically includes two or more working electrodes. Those electrodes can, for example, be placed in close proximity to each other (for example, to be adjacent and coplanar within the sensor) to provide a similar diffusion path from the inlet(s) of the sensor to each of the electrodes. Often, sensors that detect more than one analyte gas (which include more than one working electrode) can suffer cross-sensitivity of one analyte gas on at least one of the working electrodes that was designed to detect another analyte gas. One possible cause of this cross-sensitivity is lateral diffusion through a diffusion membrane and/or electrolyte to the adjacent electrode.

Several strategies have been used to address cross-sensitivity between two or more working (or other) electrodes. One strategy is the creation of a barrier to diffusion between electrodes by creating slots in a common or shared diffusion membrane between the catalysts of each electrode. The slot or slots are filled with liquid electrolyte when the sensor is filled with electrolyte. A similar approach is to place the electrodes on two separate diffusion membranes and provide for a gap between them that can likewise be filled with electrolyte to create a diffusion barrier. While the electrolyte will reduce gas diffusion, it will not completely eliminate it. In that regard, it is well known that gases will dissolve in electrolytes and migrate or diffuse therethrough, albeit at a reduced rate, than through a gas diffusion membrane used in connection with electrodes. Further, as it is often desirable to minimize the size of sensors, the distance that can be maintained between separate diffusion membranes or between separate catalyst layers on a common diffusion membrane is limited. Another approach is to compress the diffusion membrane in the area between the electrodes to create a "less permeable region". Such compression can, for example, be achieved with a bar-like structure or abutment member (for example, formed in the sensor lid) that mechanically compresses the membrane when the sensor is assembled. Although lateral diffusion is reduced by such compression, it is not totally eliminated.

SUMMARY

In one aspect, an electrochemical gas sensor includes a housing, a first working electrode within the housing having a first section of gas transfer medium and a first layer of catalyst on the first section of gas diffusion membrane, and at least a second working electrode within the housing having a second section of gas transfer medium and a second layer of catalyst on the second section of gas diffusion membrane. At least one of the first section of gas transfer medium and the second section of gas diffusion membrane includes at least one area in which the structure thereof has been irreversibly altered to limit transfer or transport of gas through the at least one of the first section of gas transfer medium or the second section of gas transfer medium toward the other of the at least one of the first section of gas transfer medium and the second section of gas transfer medium.

The first section gas transfer medium can, for example, be a first section of membrane, and the second section gas transfer medium can, for example, be a second section of membrane. In a number of embodiments, the first section of gas transfer medium is a porous gas diffusion membrane, and the second section of gas transfer medium is a porous gas diffusion membrane. The first section of membrane can, for example, be formed from a porous polymeric material through which gas can diffuse, and the second section of membrane can, for example, be formed from a porous polymeric material through which gas can diffuse. An electrolyte of the sensor can, for example, be substantially or completely excluded from the least one area in which the structure has been irreversibly altered.

Each of the first section of gas transfer medium and the second section of gas transfer medium can, for example, include an area of heat sealing to limit transfer of gas therethrough toward the other of the first section of gas transfer medium and the second section of gas transfer medium.

In a number of embodiments, the first section of gas transfer medium includes an area of heat sealing positioned toward a perimeter of the first section of gas transfer medium from the first layer of catalyst and encompassing the first layer of catalyst.

The second section of gas transfer medium can also include an area of heat sealing positioned toward a perimeter of the second section of gas transfer medium from the second layer of catalyst and encompassing the second later of catalyst.

As used herein, the term "heat sealing" refers to the application of sufficient heat to an area of a gas transfer medium (for example, a gas permeable or a gas diffusion membrane) to cause gas transfer or transport (for example, gas permeation and/or gas diffusion) to be limited or prevented through the heat sealed area. The act of heat sealing can also, in certain embodiments, be used to attach the gas transfer medium to a surface, but such an attachment need not necessarily occur during heat sealing to limit or prevent gas transfer or gas transport through an area of heat sealing.

In that regard, in a number of embodiments, the area of heat sealing of the first section of gas transfer medium can, for example, attach the first section of gas transfer medium to a surface within the electrochemical gas sensor. Similarly, the area of heat sealing of the second section of gas transfer medium can attach the second section of gas transfer medium to a surface within the electrochemical gas sensor. In several embodiments, the surface is a portion of the housing of the gas sensor. The first section of gas transfer medium of the first working electrode can be positioned adjacent to and covering a first gas inlet formed in the housing, and the second section of gas transfer medium of the second working electrode can be positioned adjacent to and covering a second gas inlet formed in the housing.

In a number of embodiments, the first section of gas transfer medium and the second section of gas transfer medium form an integral gas transfer medium (for example, a gas transfer membrane as described above). The first section of gas transfer medium and the second section of gas transfer medium can, for example, be formed separately and the at least one area of heat sealing can attach the first section of gas transfer medium to the second section of gas transfer medium to form the integral gas transfer medium.

The first section of gas transfer medium and the second section of gas transfer medium can alternatively be portions of a monolithic gas transfer medium and the at least one area of heat sealing can be formed in the monolithic gas transfer medium between the first layer of catalyst and the second layer of catalyst.

In several embodiments, the electrochemical gas sensor includes at least n working electrodes comprising at least n gas transfer medium sections, wherein at least n−1 of the gas transfer medium sections include at least one area of heat sealing limiting transfer (for example, permeation or diffusion) of gas therethrough.

An integral gas transfer medium can, for example, include at least n layers of catalyst thereon and at least n−1 areas of heat sealing.

In another aspect, an electrode assembly includes an integral gas transfer medium, a first layer of catalyst deposited on the integral gas transfer medium to form a first working electrode and at least a second layer of catalyst deposited on the integral gas transfer medium to form at least a second working electrode. The first layer of catalyst is spaced from the second layer of catalyst. The electrode assembly further includes at least one area in which the structure of the integral gas transfer medium has been irreversibly altered to limit gas transfer across the at least one area. As described above, the integral gas transfer medium comprises an integral membrane (for example, a gas permeable membrane or a gas porous membrane). In a number of embodiments, the integral gas transfer medium is a porous membrane through which gas can diffuse. The integral gas transfer medium can, for example, be formed monolithically from a material such as a membrane, which can, for example, be a porous membrane.

In a further aspect, a method of limiting gas transfer through at least one of a first membrane section of a first electrode and a second membrane section of a second electrode, includes forming at least one area of heat sealing in at least one of the first membrane section and the second membrane section.

The devices, systems and/or methods described herein, along with the attributes and attendant advantages thereof, will best be appreciated and understood in view of the following detailed description taken in conjunction with the accompanying drawings.

BRIEF DESCRIPTION OF THE DRAWINGS

FIG. 1B illustrates a top view of the housing top, cap or lid of the sensor of FIG. 1A.

FIG. 1C illustrates a bottom view of the sensor housing top, cap or lid of the sensor of FIG. 1A with two working electrodes attached thereto.

FIG. 6 illustrates experimental results for a sensor as illustrated in FIGS. 2A through 2D for the detection of hydrogen sulfide and carbon monoxide.

DETAILED DESCRIPTION

Figure 1A:
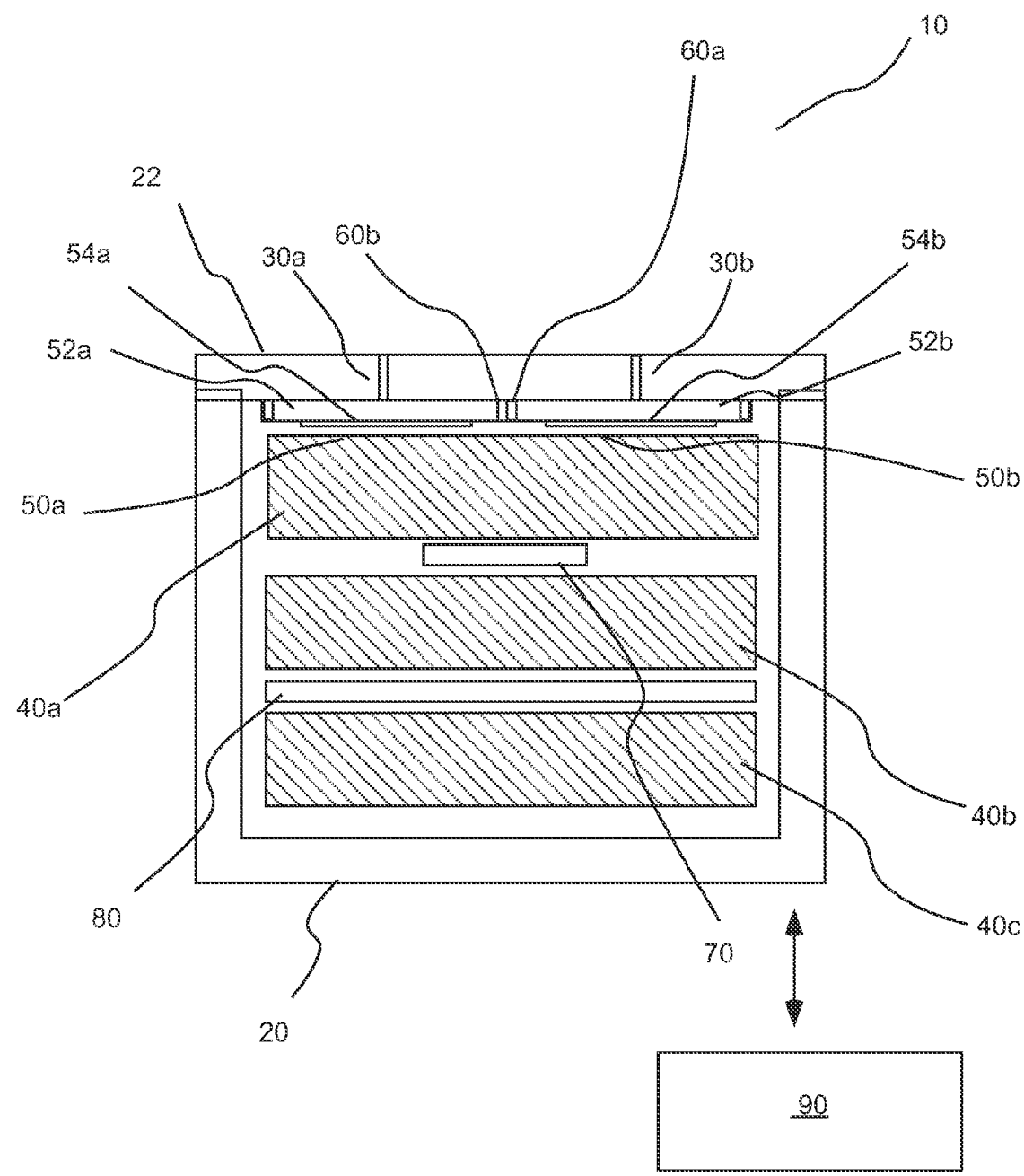
FIG. 1A illustrates a schematic, cutaway diagram of an electrochemical sensor.

As used herein and in the appended claims, the singular forms "a," "an", and "the" include plural references unless the context clearly dictates otherwise. Thus, for example, reference to "an area of heat sealing" includes a plurality of such areas of heat sealing and equivalents thereof known to those skilled in the art, and so forth, and reference to "the area of heat sealing" is a reference to one or more such areas of heat sealing and equivalents thereof known to those skilled in the art, and so forth.

In a number of embodiments, sensor electrodes include areas or layers of catalyst deposited upon a gas transfer or gas transport medium or member (that is, a media or member through which gas is transferable, transportable or movable). Driving forces that can promote such transfer include: free energy, pressure, electrical charge, temperature, and concentration. In a number of embodiments, the gas transfer medium is a gas transfer membrane through which gas can diffuse (sometimes referred to as a gas diffusion membrane) or a membrane through which gas can permeate (sometimes referred to as a gas permeable membrane). As used herein, the term "membrane" refers to a relatively thin layer of material which can, for example, be flexible. In a number of embodiments, such membranes can, for example, have an average thickness in the range of 0.5 to 20 mils. In other embodiments, thinner or thicker layers of membrane or gas transfer medium can be used.

In several embodiments, a sensor electrode system includes multiple electrodes as described above. One or more processes other than mechanical deformation (such as heating/heat sealing, chemical reaction and/or material deposition) are used to disrupt (for example, collapse) the structure or morphology of the gas transport medium, thereby creating a region or a gas transfer barrier in the disrupted areas. For example, heat sealing of at least one gas transfer medium (for example, a gas diffusion membrane) of the electrodes can be used to collapse pore structure and create one or more areas or regions through which gas cannot transfer or move (for example, diffuse and/or permeate). The areas through which gas cannot transfer (heat sealed areas) are formed between areas of different catalyst layers which define separate electrodes to limit or prevent transfer of gas from the catalyst layer of one electrode to the catalyst layer of another electrode.

In addition to heat sealing, a number of other methods can be used to create areas in which gas transfer is limited or prevented. For example, metal deposition can be effected within the pores of an area of a porous medium or membrane to prevent gas transfer therethrough. Such metal deposition can, for example, be effected by the reduction of a metal ion from solution within the medium to "fill" pores and produce a gas transfer barrier. Further, precipitation of a solid from a liquid solution that is within the pores can be effected to "fill" pores and created a gas transfer barrier. Particles of an inert material (for example, polytetrafluoroethylene or PTFE powder) can be infiltrated into pores by, for example, pulling a vacuum on an opposite side of a membrane. In a number of other embodiments, pores can be filled or blocked with a polymeric material. For example, a liquid epoxy can be allowed to penetrate the pores and subsequently cured to harden the epoxy material and produce a transfer barrier. Curing can, for example, be accelerated with heat and/or UV radiation. Alternatively, a polymer that has been melted to a liquid phase can be allowed to penetrate pores and subsequently cooled to produce a transfer barrier. Further, a liquid monomer can be allowed to penetrate the pores and subsequently be polymerized within the pores to produce a transfer barrier.

Unlike mechanical compression of a membrane, which, as described above, has been used to create areas of limited diffusion between electrodes in a gas diffusion membrane in a number of currently available sensors, the present gas transport barriers or areas of limited gas transport are created at the time of manufacture and do not require an ongoing application of pressure or other action to maintain the gas transport barriers. In the case of mechanical compression of a membrane, gas transfer can increase or recover through the area of compression upon removal of mechanical compression. To the contrary, the gas transfer barriers are formed via non-elastic, substantially permanent and/or permanent physical and/or chemical changes in the medium or membrane (for example, a change in composition, morphology and/or pore structure) that is not reversible under the conditions of normal use of a sensor. No continuing action (such as, for example, maintenance of mechanical compression) is required to maintain the gas transport barriers or areas of limited gas transport in the mediums of membranes hereof during normal use of the sensors hereof.

Moreover, unlike a number of currently available sensors in which one or more sections of a membrane are removed to allow liquid electrolyte to fill the void, the gas transport barriers hereof substantially or completely exclude liquid electrolyte therefrom. As discussed above, the presence of electrolyte can reduce gas diffusion somewhat but cannot eliminate it as gases will dissolve in electrolytes and migrate or diffuse therethrough. Unlike removal of a section of membrane, in the case of the gas transfer barriers hereof, the gas transfer barrier or area of limited diffusion remains integral with or attached to the medium or membrane, but is irreversibly changed to substantially or completely prevent gas transport therethrough. In the case or currently available sensors wherein a section of the membrane is removed and electrolyte is allowed to fill the void to serve as a partial barrier, that partial barrier itself may not be permanent. For example, in low relative humidity or RH conditions, the volume of an electrolyte will decrease and the electrolyte will be preferentially distributed within the wicking material and not within the void section of the membrane. In such a case, the partial barrier is effectively removed and the sensor can exhibit cross-sensitivity depending on the environmental conditions.

Unlike such currently available sensors, the irreversible gas transport barriers hereof are independent of environmental changes.

In several embodiments, at least one electrode is placed adjacent to at least one other electrode. Separate gas transfer media of the electrodes can contact each other or they can be separated by a space. Each of the electrodes can, for example, be placed adjacent to each other and generally in the same plane as each other. For example, each electrode can be attached (for example, by heat sealing) to a common, generally planar surface. The electrodes need not be planar, however. Two electrodes can, for example, be attached to a curved surface.

Each electrode can include a region or area of heat sealing (and/or other gas transport or gas transfer disruption as described herein) spaced from the catalyst layer of the electrode toward the perimeter of the gas transfer medium of the electrode to limit or prevent transfer of gas to the catalyst layer of the other electrode through the heat sealed region or area. The catalyst layer of a particular electrode can, for example, be completely surrounded by an area of heat sealing (for example, around the perimeter of the gas transfer medium) to completely prevent transfer of gas out of the edge of the gas transfer medium toward the catalyst layer of another electrode.

In a number of embodiments, an electrode assembly is formed as an integral medium or member (for example, an integral or single membrane) to include more than one electrode. As used herein, the, the term "integral" refers to a medium or member (for example, a membrane) formed as a unit. The integral medium can be formed from separate media sections that are, for example, heat sealed together to provide an area of heat sealing between catalyst layers on each medium section. One or more catalyst layers or areas of catalyst can be surrounded by an area of, for example, heat sealing to create an isolated area within the area of heat sealing into or out of which gas cannot transfer (through the medium). In such an isolated area, gas transfer (for example, diffusion and/or permeation) can occur through the medium within the isolated area but not laterally out of the edge of the area to an adjacent area. The integral medium or member can also be formed from a single, monolithic medium or member (for example a membrane wherein one or more areas of, for example, heat sealing are formed in the medium or member to define isolated sections or areas therein.

In a number of representative embodiments of electrochemical sensors described below, gas diffusion membranes were used in forming sensor electrodes and heat sealing was used to create gas transfer/diffusion barriers. As clear to one skilled in the art, other gas transfer media can be used in forming such electrodes wherein heating/heat sealing and/or other methods can create isolated areas across which gas transfer in substantially limited or prevented.

FIG. 1A illustrates a schematic diagram of an electrochemical sensor 10 including a housing 20 having a first gas inlet 30a and a second gas inlet 30b for entry of analyte gases into sensor 10. Electrolyte saturated wick materials 40a, 40b and 40c separate working electrodes 50a and 50b from reference electrode(s) 70 and counter electrode(s) 80 within sensor 10 and/or provide ionic conduction therebetween via the electrolyte absorbed therein. Electronic circuitry 90 as known in the art is provided, for example, to maintain a desired potential between working electrodes 50a and 50b and reference electrode(s) 70 and to process an output signal from sensor 10.

In one embodiment, sensor 10 includes two working electrodes 50a and 50b that are located to be generally coplanar within sensor housing 20. In the illustrated embodiment, first working electrode 50a is formed by depositing a first layer of catalyst 54a on a first diffusion membrane 52a (using, for example, catalyst deposition techniques known in the sensor arts). Second working electrode 50b is formed by depositing a second layer of catalyst 54b on a second diffusion membrane 52b (using, for example, catalyst deposition techniques known in the sensor arts). Each of working electrode 50a and working electrode 50b can be attached (for example, via heat sealing) to an inner surface of a top, cap or lid 22 of housing 20. In the embodiment of FIGS. 1B and 1C, catalyst layer 54a and 54b of each of first diffusion membrane 52a and second diffusion membrane 52b, respectively, is diffusionally separated from the other of first catalyst layer 54a and second catalyst layer 54b via first area of heat sealing 60a and second area of heat sealing 60b. First area of heat sealing 60a and second area of heat sealing 60b also operate to attach first working electrode 50a and second working electrode 50b to housing lid 22.

Heating of the membranes during heat sealing collapses the pore structure of membranes 52a and 52b, thereby creating a non-porous or non-permeable region or a diffusion barrier in areas of heat sealing 60a and 60b. In several studies, such a collapse was evidenced by a change in the appearance of the membrane from white to translucent after the heat sealing process. Unlike previous methodologies for creating gas transfer (for example, diffusion barriers) such as mechanical compression, heat sealing can substantially (or even completely) and irreversibly prevent lateral gas transfer/diffusion through the gas transfer/diffusion barrier across the area of heat sealing. This result is accomplished, for example, without the use of complicated abutment members required to compress any area of the diffusion membrane.

First working electrode 50a is attached to lid 22 to be adjacent to and cover first gas inlet 30a. Second working electrode 50b is attached to lid 22 to be adjacent to and cover second gas inlet 30b.

Figure 2A:
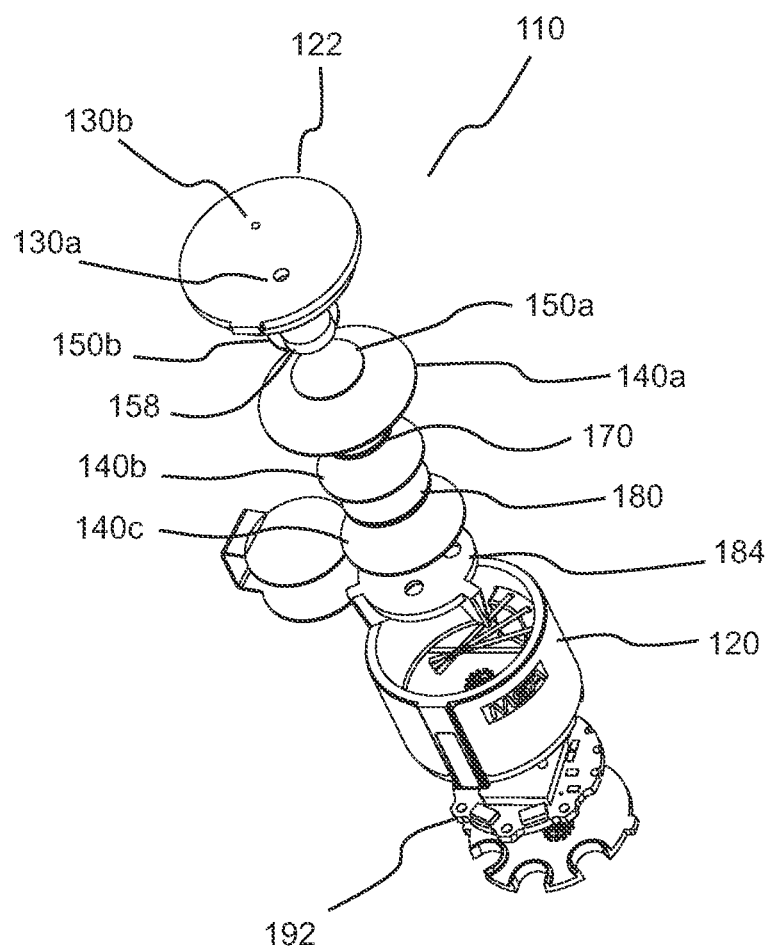
FIG. 2A illustrates a perspective, exploded or disassembled view of a sensor including multiple working electrodes.

FIG. 2A illustrates an embodiment of a sensor 110 that is very similar in design and operation to sensor 10. Like elements of sensor 110 are numbered similarly to corresponding elements of sensor 110 with the addition of 100 to the reference numbers of the elements of sensor 110. As illustrated in FIG. 2A, reference electrode 170, counter electrode 180 and electrolyte absorbent wicks 140a, 140b and 140c are supported within housing 120 via a support member 184. A printed circuit board 192 is connected to housing 120 and can form a part of the electronic circuitry of sensor 110.

Figure 2D:
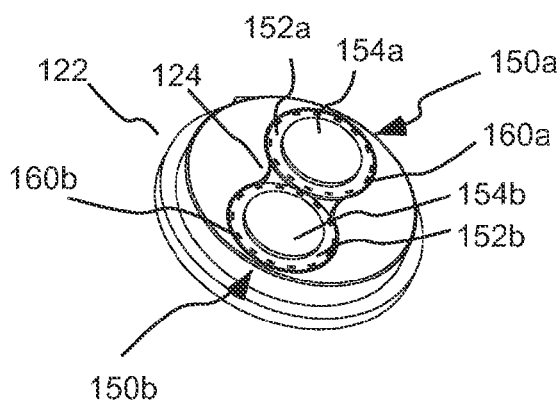
FIG. 2D illustrates a perspective view of the sensor housing lid of the sensor of FIG. 2A with two working electrodes attached thereto.
Figure 2C:
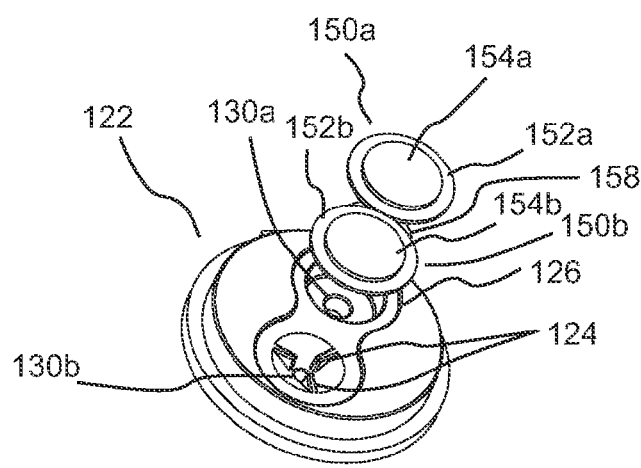
FIG. 2C illustrates a perspective view of the sensor housing lid of the sensor of FIG. 2A with two working electrodes in alignment for attachment thereto.
Figure 2B:
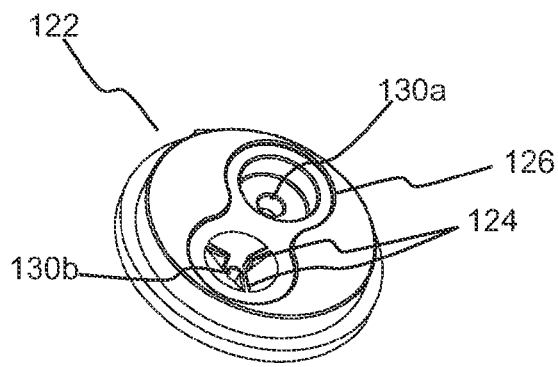
FIG. 2B illustrates a perspective view of the sensor housing lid of the sensor of FIG. 2A.

As, for example, illustrated in FIGS. 2A through 2D, a housing lid 122 includes a first gas inlet 130a and a second gas inlet 130b. First inlet 130a can, for example, be for use in connection with first electrode 150a for an analyte gas such as carbon monoxide. Catalyst layer 154a (which can, for example, include platinum) of first electrode 150a can, for example, be protected from poisoning with, for example, a second analyte gas such as hydrogen sulfide by a filter 158 (see FIG. 2A). Second inlet 130b is for use in connection with another analyte gas (for example, hydrogen sulfide). In the case of hydrogen sulfide, for example, choice of a second catalyst layer including, for example, iridium required no filter. However, filters can be used in connection with each gas inlet of a sensor. As illustrated in FIGS. 2B and 2C, support members 124 can be provided to support second electrode 150b adjacent second inlet 130b.

In the illustrated embodiment, the inner surface of housing lid 122 includes a seating 126 formed therein which is dimensioned to adjacently seat and position first electrode 150a and second electrode 150b. As illustrated in FIG. 2D, the perimeters of first diffusion membrane 152a and second diffusion membrane 152b are heat sealed to create areas of heat sealing 160a and 160b, respectively (dashed lines in FIG. 2D). As described above, areas of heat sealing 160a and 160b fully encompass first catalyst layer 154a and second catalyst layer 154b, respectively.

First gas diffusion membrane 152a and second gas diffusion membrane 152b further operate to minimize or prevent leakage of electrolyte from first gas inlet 130a and second gas inlet 130b, respectively. In the case of an aqueous electrolyte, the material(s) (which can be the same or different) of the gas diffusion membranes can be generally hydrophobic in nature to minimize or eliminate any flow of the aqueous electrolyte therethrough. In the case of a non-aqueous (for example, organic) electrolyte, the material of the gas diffusion membranes can be generally oleophobic in nature to minimize or eliminate any flow of the non-aqueous electrolyte therethrough. The material(s) can also be hydrophobic and oleophobic. Such materials are referred to as "multiphobic". The materials can also be chemically or otherwise treated to minimize or eliminate liquid electrolyte flow or leakage therethrough.

In general, the term "hydrophobic" as used herein refers to materials that are substantially or completely resistant to wetting by water at pressures experienced within electrochemical sensors (and thus limit flow of aqueous electrolyte therethrough in the case of the extending member). In general, the term "oleophobic" as used herein refers to materials that are substantially or completely resistant to wetting by low-surface tension liquids such as non-aqueous electrolyte systems at pressures experienced within electrochemical sensors (and thus limit flow of non-aqueous electrolyte therethrough in the case of the extending member). As used herein, the phrase "low-surface tension liquids" refers generally to liquids having a surface tension less than that of water. Hydrophobic, oleophobic, and multiphobic materials for use in electrodes are, for example, discussed in U.S. Pat. No. 5,944,969.

Gas diffusion membranes for use herein can, for example, be formed from polymeric materials such as, but not limited to, polytetrafluoroethylene (for example, GORETEX®), polyethylene or polyvinylidene fluoride (PVDF). Such polymeric materials can, for example, include a pore structure therein that provides for gas diffusion therethrough.

Figure 3A:
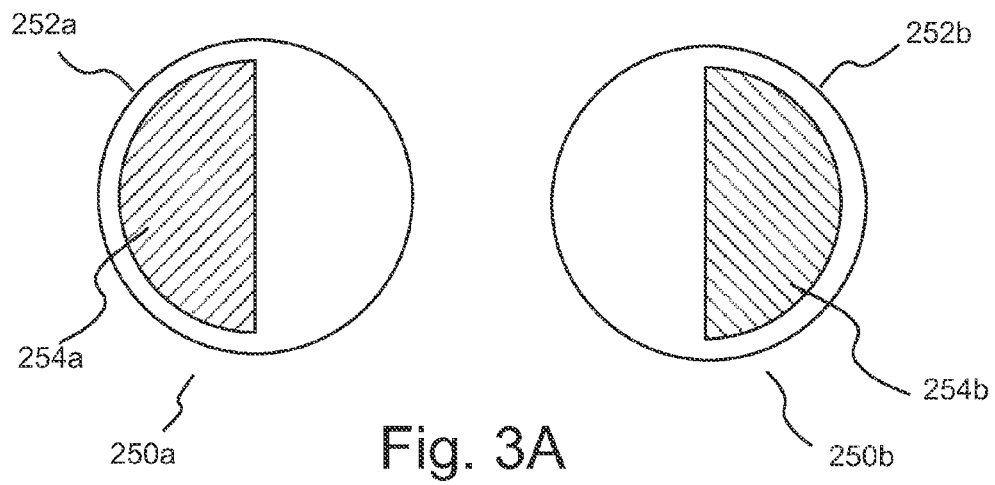
FIG. 3A illustrates two electrodes which are formed on separate sections of gas diffusion membranes.
Figure 3B:
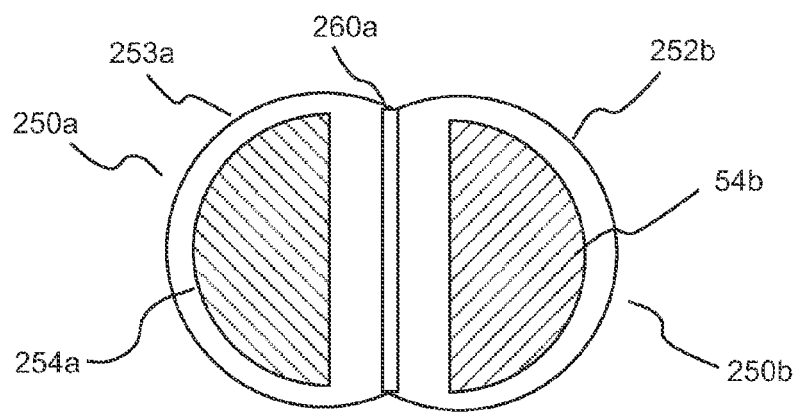
FIG. 3B illustrates connection of the two electrodes of FIG. 3A via an area of heat sealing, which prevents diffusion directly through the diffusion membrane between the catalysts of the two electrodes.
Figure 3C:
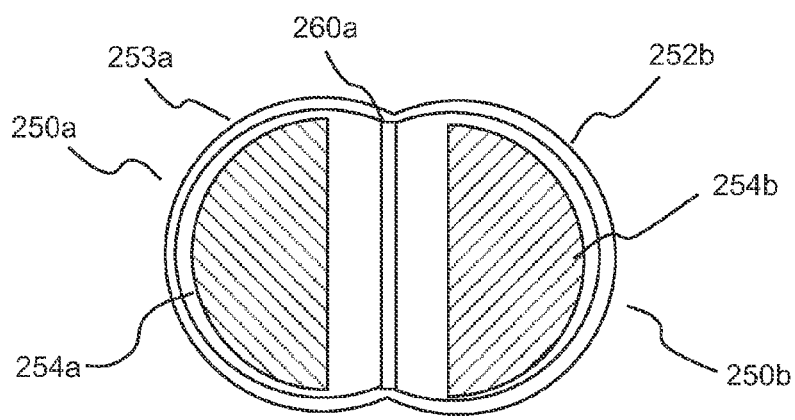
FIG. 3C illustrates connection of the two electrodes of FIG. 3A via an area of heat sealing and fully or completely surrounding or encompassing the catalyst layers of the electrodes with an area of heat sealing, which prevents diffusion directly through the diffusion membrane between the catalysts of the two electrodes and through the edges of the diffusion membranes and into the catalyst.

In the embodiment of FIGS. 3A through 3C, first working electrode 250a is formed by depositing a first layer of catalyst 254a on a first diffusion membrane 252a. Second working electrode 250b is formed by depositing a second layer of catalyst 254b on a second diffusion membrane 252b. In the embodiment of FIGS. 3A through 3C, first diffusion membrane 252a and second diffusion membrane 252b are connected and diffusionally separated or isolated via an area of heat sealing 260a, which operates to form an integral, single membrane. In that regard, diffusion membrane sections 252a and 252b are overlapped or placed adjacent to each other and connected or attached by heating to create area of heat sealing 260a. The heat sealing process prevents diffusion directly through the integral diffusion membrane between first catalyst layer 254a and second catalyst layer 254b.

In the case of certain materials, such as certain polytetrafluoroethylene or PTFE materials, heat sealing alone may not be sufficient to attached two sections of gas diffusion membrane to form an integral membrane. One or more other processes such as mechanical etching, corona etching and/or chemical etching may be required to from a sufficient attachment. In certain other material, heat sealing alone can be used to attach two sections of gas diffusion membrane (as well as to create an area through which diffusion is limited or prevented). As also described above, heat sealing can also be used to attach the gas diffusion membrane to a surface. Even in the case of PTFE, heat sealing alone can be used to attach the gas diffusion membrane to a surface as long as the surface includes "imperfections" suitable to create anchoring points.

In the embodiment of FIG. 3B, it is possible for gas to diffuse out of the edge of one of first diffusion membrane section 252a and second diffusion membrane section 252b, enter the electrolyte and diffuse therethrough, and then diffuse into the edge of the other of first diffusion membrane section 252a and second diffusion membrane section 252b. Such a diffusion path can be eliminated by providing an area of heat sealing around the entire perimeter of the integral diffusion membrane (including first diffusion membrane section 252a and second diffusion membrane section 252b). As diffusion of gas through electrolyte is much slower than through an electrode diffusion membrane, it may not be necessary to completely heat seal the perimeter in certain embodiments to adequately limit gas diffusion and resulting cross-sensitivity.

Figure 4A:
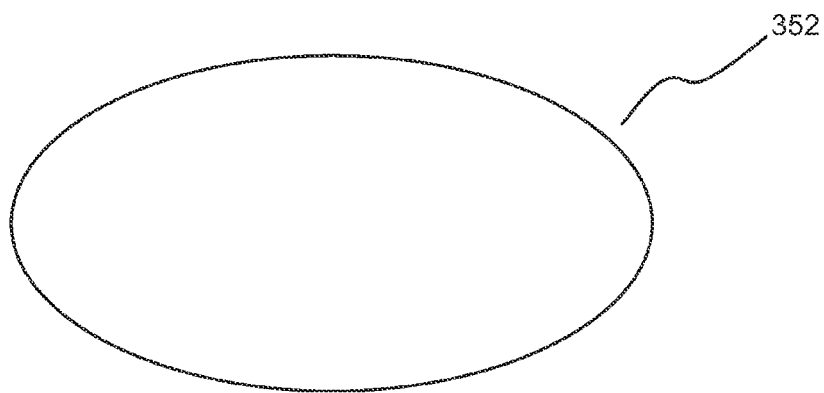
FIG. 4A illustrates a single gas permeable diffusion membrane for formation of multiple electrodes thereon.
Figure 4B:
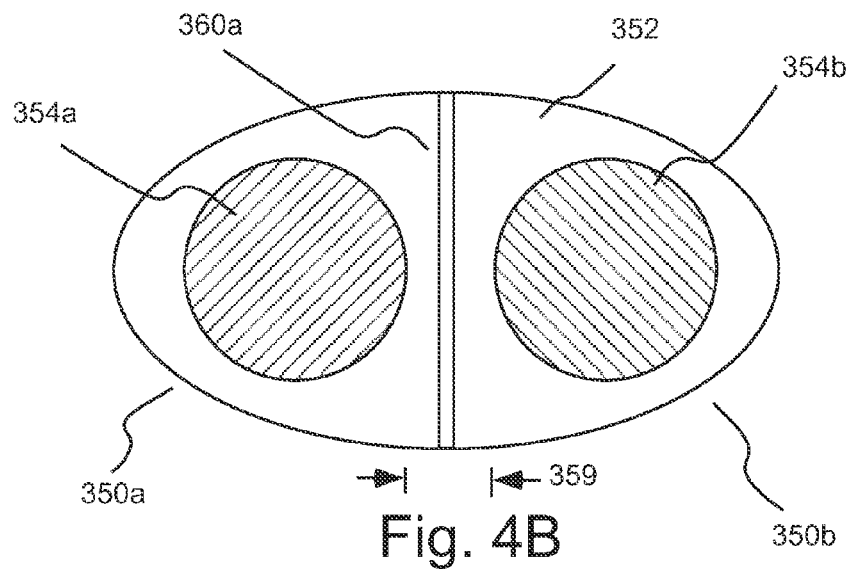
FIG. 4B illustrates an electrode system or assembly including two catalyst layers separated by a space on the single, monolithic gas diffusion membrane of FIG. 4A wherein an area of heat sealing is positioned in the space between the two catalyst layers to prevent diffusion between the catalyst layers.
Figure 4C:
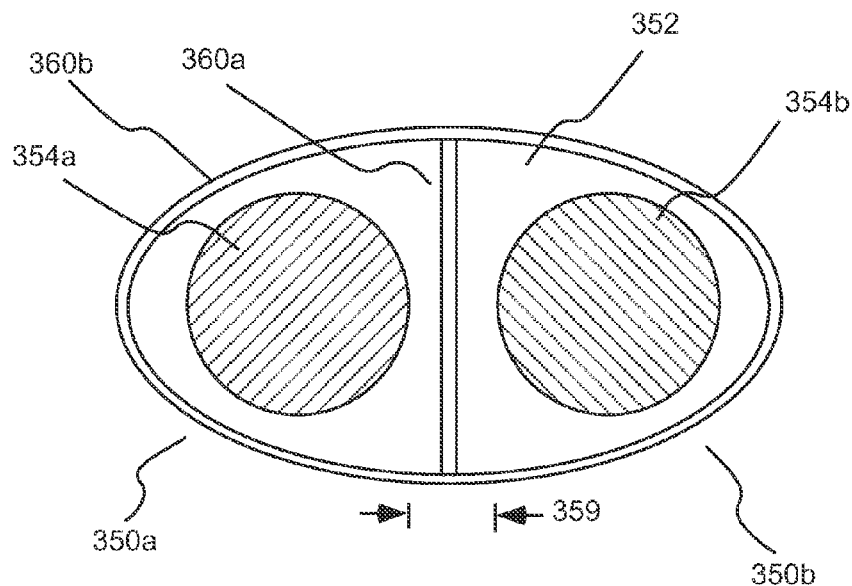
FIG. 4C illustrates the electrode system of FIG. 4B wherein the perimeter of the gas diffusion membrane is heat sealed.

As illustrated in FIGS. 4A through 4C, an electrode assembly including two working and/or other electrodes 350a and 350b (see FIG. 4B) can be formed on a single, monolithic diffusion membrane 352 by forming or depositing two catalyst layers 354a and 354b on diffusion membrane 352. Catalyst layers 354a and 354b are separated by a distance or space 359. After depositing catalyst layers 354a and 354b, an area of heat sealing 360a is formed in space 359 between catalyst layers 354a and 354b, thereby preventing diffusion through diffusion membrane 352 across area 360a (which extends over the entire width of membrane 352 in the illustrated embodiment to separate catalyst layer 354a from catalyst layer 354b. As illustrated in FIG. 4C an area of heat sealing 360b can also be provided around the perimeter of diffusion membrane 352 to prevent diffusion of gas from the edges of membrane 352.

Figure 5:
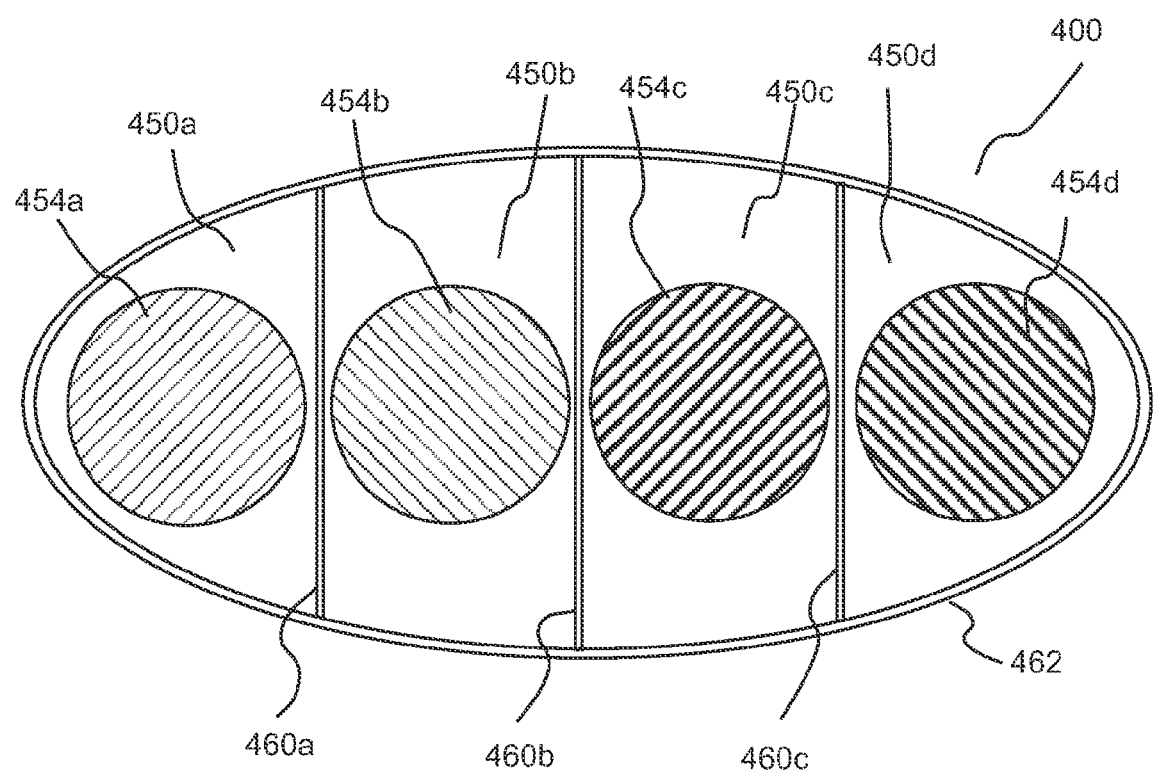
FIG. 5 illustrates the formation of an electrode assembly including four catalyst layers separated by spaces on a single, monolithic gas diffusion membrane wherein an area of heat sealing is positioned in the space between adjacent catalyst layers to prevent diffusion between the catalyst layers of the electrodes.

As is clear to one skilled in the art, virtually any number of electrodes can be formed on an integral membrane either (i) by connecting a plurality of membrane sections via heat sealing to create an integral membrane including (at least partially) diffusionally isolated electrodes thereon or (ii) by dividing a single, monolithic membrane into sections by heat sealing to create an integral membrane including (at least partially) diffusionally isolated electrodes). FIG. 5, for example, illustrates an electrode assembly 400 including four electrodes 450a, 450b, 450c and 450d, including catalyst layers 454a, 454b, 454c and 454d, respectively, with areas of heat sealing 460a, 460b and 460c therebetween to prevent lateral diffusion across the membrane between electrodes 450a, 450b, 450c and 450d. In a number of embodiments similar to FIG. 5, one can, for example, form n electrodes with at least n−1 areas of heat sealing therebetween. As also illustrated in FIG. 5, and as discussed above, the perimeter of gas diffusion membrane 352 can be diffusionally sealed via an area of heat sealing 462.

A sensor as described in FIGS. 2A through 2D was used in several studies for the detection/measurement of carbon monoxide (CO) and hydrogen sulfide ($H_2S$). The electrodes were sealed to the sensor lid by heat sealing as described in connection with FIGS. 2A through 2D. The catalyst on the CO working electrode was platinum, while the catalyst on the $H_2S$ working electrode was iridium. A filter for scrubbing $H_2S$ from the inlet stream was included over the CO electrode. The iridium catalyst used for the $H_2S$ detection does not support CO oxidation, therefore, no filter was needed under the $H_2S$ gas inlet. Because $H_2S$ passing through the gas inlet associated with the CO electrode is removed by filter 158, $H_2S$ should not diffuse through the gas diffusion membrane of the CO electrode toward the $H_2S$ electrode. Further, as all CO gas should react at the catalyst layer of the CO electrode, CO should not diffuse through the gas diffusion membrane of the CO electrode toward the $H_2S$ electrode. As there is no filter for CO on the gas inlet associated with the $H_2S$ electrode, CO gas can pass therethrough to the $H_2S$ electrode. However, the heat sealed perimeter gas diffusion membrane of the $H_2S$ electrode prevents diffusion of CO gas therethrough toward the CO electrode. As all $H_2S$ gas should react at the catalyst layer of the $H_2S$ electrode, $H_2S$ should not diffuse through the gas diffusion membrane of the $H_2S$ electrode toward the CO electrode.

An example of a typical response of such a sensor is shown in FIG. 6. Both the CO channel and the $H_2S$ channel responses are illustrated in FIG. 6. In the studies, each channel baseline (sensor output in the absence of analyte gases) was measured for 2 minutes. Then, 40 ppm $H_2S$ was applied for 10 minutes followed by air being applied for 5 minutes. The application of air cleared the sensor of $H_2S$ analyte gas and returned the baseline to near zero current. Finally, 100 ppm CO was applied for 10 minutes, followed by application of 5 minutes of air.

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of limiting gas transfer between electrodes in an electrochemical gas sensor, the electrochemical gas sensor including a housing, and a first working electrode within the housing, the first working electrode including a first section of gas transfer medium including a first layer of catalyst thereon, the electrochemical gas sensor further including at least a second working electrode within the housing, the second working electrode including a second section of gas transfer medium including a second layer of catalyst thereon, the method comprising: irreversibly altering at least one area of at least one of the first section of gas transfer medium and the second section of gas transfer medium so that the structure of the at least one area is irreversibly altered via at least one of heat sealing, chemical reaction or material deposition to prevent gas transfer through the at least one of the first section of gas transfer medium or the second section of gas transfer medium toward the other of the at least one of the first section of gas transfer medium and the second section of gas transfer medium in the absence of mechanical compression of the at least one area.

2. An electrochemical gas sensor comprising: a housing, and a first working electrode within the housing, the first working electrode comprising a first section of gas transfer medium comprising a first layer of catalyst thereon, the electrochemical gas sensor further comprising at least a second working electrode within the housing, the second working electrode comprising a second section of gas transfer medium comprising a second layer of catalyst thereon, at least one of the first section of gas transfer medium and the second section of gas transfer medium comprising at least one area in which the structure thereof has been irreversibly altered via at least one of heat sealing, chemical reaction or material deposition to prevent gas transfer through the at least one of the first section of gas transfer medium or the second section of gas transfer medium toward the other of the at least one of the first section of gas transfer medium and the second section of gas transfer medium in the absence of mechanical compression of the at least one area.

3. The electrochemical gas sensor of claim 2 wherein the first section gas transfer medium is a first section of membrane and the second section gas transfer medium is a second section of membrane.

4. The electrochemical gas sensor of claim 3 comprising at least n working electrodes comprising at least n membrane sections, wherein n is an integer greater than or equal to 2, and wherein at least n−1 of the membrane sections comprise at least one area of heat sealing preventing transfer of gas therethrough in the absence of mechanical compression.

5. The electrochemical gas sensor of claim 3 wherein the first section of membrane is formed from a porous polymeric material through which gas can diffuse and the second section of membrane is formed from a porous polymeric material through which gas can diffuse.

6. The electrochemical gas sensor of claim 2 wherein an electrolyte of the sensor is excluded from the least one area.

7. The electrochemical gas sensor of claim 3 wherein each of the first section of membrane and the second section of membrane includes an area of heat sealing to prevent transfer of gas therethrough toward the other of the first section of membrane and the second section of membrane in the absence of mechanical compression.

8. The electrochemical gas sensor of claim 3 wherein the first section of membrane comprises an area of heat sealing positioned toward a perimeter of the first section of membrane from the first layer of catalyst and encompassing the first layer of catalyst to prevent transfer of gas therethrough in the absence of mechanical compression.

9. The electrochemical gas sensor of claim 8 wherein the second section of membrane comprises an area of heat sealing positioned toward a perimeter of the second section of membrane from the second layer of catalyst and encompassing the second layer of catalyst to prevent transfer of gas therethrough in the absence of mechanical compression.

10. The electrochemical gas sensor of claim 9 wherein the area of heat sealing of the first section of membrane attaches the first section of membrane to a surface within the electrochemical gas sensor.

11. The electrochemical gas sensor of claim 10 wherein the area of heat sealing of the second section of membrane attaches the second section of membrane to a surface within the electrochemical gas sensor.

12. The electrochemical gas sensor of claim 11 wherein the surface is a portion of the housing of the gas sensor and the first section of membrane of the first working electrode is positioned adjacent to and covering a first gas inlet formed in the housing and the second section of membrane of the second working electrode is positioned adjacent to and covering a second gas inlet formed in the housing.

13. The electrochemical gas sensor of claim 3 wherein the first section of membrane and the second section of membrane form an integral membrane.

14. The electrochemical gas sensor of claim 13 wherein the first section of membrane and the second section of membrane are formed separately and at least one area of heat sealing attaches the first section of membrane to the second section of membrane to form the integral membrane.

15. The electrochemical gas sensor of claim 13 wherein the first section of membrane and the second section of membrane are portions of a monolithic membrane and at least one area of heat sealing is formed in the monolithic membrane between the first layer of catalyst and the second layer of catalyst.

16. The electrochemical gas sensor of claim 13 wherein the integral membrane comprises at least n layers of catalyst thereon and at least n−1 areas of heat sealing, wherein n is an integer greater than or equal to 2.

17. An electrode assembly comprising an integral gas transfer medium, a first layer of catalyst deposited on the integral gas transfer medium to form a first working electrode and at least a second layer of catalyst deposited on the integral gas transfer medium to form at least a second working electrode, the first layer of catalyst being spaced from the second layer of catalyst, the electrode assembly further comprising at least one area in the integral gas transfer medium which is positioned between the first layer of catalyst and the second layer of catalyst and in which the structure of the integral gas transfer medium has been irreversibly altered to prevent gas transfer across the at least one area in the absence of mechanical compression thereof via at least one of heat sealing, chemical reaction or material deposition.

18. The electrode assembly of claim 17 wherein the integral membrane is formed from a porous polymeric material through which gas can diffuse.

19. The electrode assembly of claim 17 wherein the integral gas transfer medium comprises an integral membrane.

20. The electrode assembly of claim 19 wherein heat sealing is used to alter the structure of the integral membrane to prevent gas transfer across the at least one area in the absence of compression thereof.

* * * * *